United States Patent
Kamata et al.

(10) Patent No.: US 7,659,413 B2
(45) Date of Patent: Feb. 9, 2010

(54) (METH) ACRYLOYL GROUP-CONTAINING OXETANE COMPOUND AND PRODUCTION METHOD THEREOF

(75) Inventors: Hirotoshi Kamata, Kanagawa (JP); Katsutoshi Morinaka, Kanagawa (JP); Hiroshi Uchida, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 24 days.

(21) Appl. No.: 10/588,072

(22) PCT Filed: Feb. 9, 2005

(86) PCT No.: PCT/JP2005/002381

§ 371 (c)(1),
(2), (4) Date: Jul. 31, 2006

(87) PCT Pub. No.: WO2005/075445

PCT Pub. Date: Aug. 18, 2005

(65) Prior Publication Data

US 2007/0060760 A1    Mar. 15, 2007

Related U.S. Application Data

(60) Provisional application No. 60/545,488, filed on Feb. 19, 2004.

(30) Foreign Application Priority Data

Feb. 10, 2004    (JP) .............................. 2004-032867

(51) Int. Cl.
*C07D 407/00* (2006.01)
(52) U.S. Cl. ..................................... 549/510
(58) Field of Classification Search .................. 549/510
See application file for complete search history.

(56) References Cited

U.S. PATENT DOCUMENTS 6,166,100 A    12/2000  Hiwara et al.
6,953,862 B2 *  10/2005  Musa .......................... 549/510

FOREIGN PATENT DOCUMENTS

| EP | 0 867 443 A2 | 9/1998 |
| JP | 7-17958 A | 1/1995 |
| JP | 11-130766 A | 5/1999 |
| JP | 2000-26444 A | 1/2000 |
| JP | 2000-63371 A | 2/2000 |
| JP | 2000-336082 A | 12/2000 |
| JP | 2000-336133 A | 12/2000 |
| JP | 2001-31664 A | 2/2001 |
| JP | 2001-31665 A | 2/2001 |
| JP | 2003-137877 A | 5/2003 |
| JP | 2003-137878 A | 5/2003 |
| JP | 2003-201286 A | 7/2003 |

OTHER PUBLICATIONS

Mikito et al, Abstract, JP11246541, (1999). Best Availible.*
Takashi Ishizone, et al., "Protection and Polymerization of Functional Monomers. 29. Syntheses of Well-Defined Poly[(4-vinylphenyl) acetic acid], Poly[3-(4-vinylphenyl)propionic acid], and Poly(3-vinylbenzoic acid) by Means of Anionic Living Polymerizations of Protected Monomers Bearing Bicyclic Ortho Ester Moieties", Macromolecules, 1999, pp. 1453-1462, vol. 32, No. 5.
Examination Report from EPO dated May 28, 2008.

* cited by examiner

*Primary Examiner*—Janet L. Andres
*Assistant Examiner*—Raymond Covington
(74) *Attorney, Agent, or Firm*—Sughrue Mion, PLLC

(57) ABSTRACT

The present invention relates to an oxetane compound containing a (meth)acryloyl group represented by formula (1) having a high copolymerizability with compounds containing a (meth)acryloyl group, and to a production method of an oxetane compound containing a (meth)acryloyl group which is characterized by reacting an isocyanate compound having a (meth)acryloyl group represented by formula (5) with an oxetane compound containing a hydroxyl group represented by formula (6).

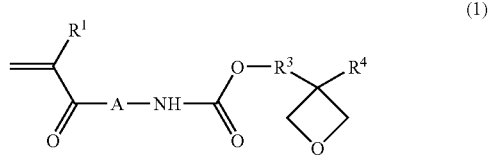

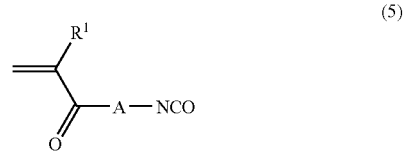

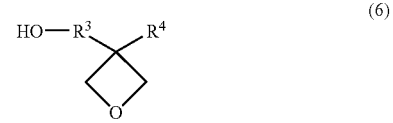

(In the formula, $R^1$ represents a hydrogen atom or a methyl group, A represents —$OR^2$— or a bond, $R^2$ represents a divalent hydrocarbon group which may contain an oxygen atom in the main chain, $R^3$ represents a linear or branched alkylene group having 1 to 6 carbon atoms, and $R^4$ represents a linear or branched alkyl group having 1 to 6 carbon atoms.)

6 Claims, 2 Drawing Sheets

(METH) ACRYLOYL GROUP-CONTAINING OXETANE COMPOUND AND PRODUCTION METHOD THEREOF

CROSS-REFERENCE TO THE RELATED APPLICATIONS

This is an application filed pursuant to 35 U.S.C. Section 111(a) with claiming the benefit of U.S. Provisional application Ser. No. 60/545,488 filed Feb. 19, 2004, under the provision of 35 U.S.C. Section 111(b), pursuant to 35 U.S.C. Section 119(e) (1).

TECHNICAL FIELD

The present invention relates to a novel oxetane compound containing a (meth)acryloyl group and production method thereof. The oxetane compound of the present invention has a high copolymerizability with other compounds containing ethylenic unsaturated groups and is useful for synthesis of various acrylic copolymers having an oxetanyl group in the side chain which can be used for various reactions such as ring-opening polymerization reaction and addition reaction.

BACKGROUND ART

An oxetane compound, which has a polarized bond between carbon and oxygen, is a four-membered ring ether compound which exhibits a high reactivity. The compound has an excellent property of exhibiting a higher polymerization rate particularly in photo-induced or thermally induced cationic polymerization than an epoxy compound.

Moreover, unlike epoxy compounds which have mutagenicity, safety for the human body is a major characteristic of oxetane compounds.

Recently, studies on ring-opening reactions other than cationic polymerization have been advancing. For example, Kougyou Zairyou (Engineering Materials) Vol. 49, No. 6 pages 53-60 (2001) illustrates reactions of oxetane compound with acyl halide compound, thiol compound, phenol compound and carboxylic acid, and suggests possibility of a new heat-curable resin. Oxetane compounds are being much anticipated to be industrially used in a wider range.

Many other oxetane compounds have been reported. For instance, an oxetane compound having a bisphenol skeleton as substitution for epoxy resin (JP-A-11-130766), an oxetane compound having a fluorene skeleton (JP-A-2000-336082), an oxetane compound having a novolak skeleton (JP-A-2000-336133), an oxetane compound having a naphthalene skeleton (JP-A-2001-31664) and a polyfunctional oxetane compound having a biphenyl skeleton (JP-A-2001-31665) have been disclosed.

An oxetane compound having an ethylenically unsaturated group for the purpose of introducing an oxetanyl group into the side chain of a vinyl-based copolymer is disclosed (JP-A-7-17958 and JP-A-2000-26444).

Further, synthesis methods of a monomer having both an oxetanyl group and a (meth)acryl group are disclosed in JP-A-2000-63371, and JP-A-2003-201286, JP-A-2003-137878 and JP-A-2003-137877.

DISCLOSURE OF THE INVENTION

However, since ethylenically unsaturated groups these oxetane compounds contain are alkenyl ethers, the compounds exhibits low copolymerizability with acryloyl groups or methacryloyl groups (hereinafter, both groups are collectively referred to as "(meth)acryloyl group(s)" in the present specification) which are the most generally employed as radically polymerizable monomers, and therefore it is difficult to efficiently introduce an oxetanyl group into the side chain of a vinyl-based or an acryl-based copolymer.

Further, an oxetane compound having both an oxetanyl group and a (meth)acryl group is improved in polymerizability, however, a problem still remains in that, with its adhesiveness to other polymers or materials being poor, its practical properties are low.

Accordingly, an object of the present invention is to provide a novel oxetane compound which has high practical properties, excellent in copolymerizability with compounds containing (meth)acryloyl groups and production method thereof.

As a result of ardent research, the present inventors found out that an oxetane compound containing a (meth)acryloyl group can be easily obtained by reacting an isocyanate compound containing a (meth)acryloyl group with an oxetane compound containing a hydroxyl group and that such a compound having a urethane bond is excellent in practical properties such as adhesiveness with other materials. Based on these findings, the present inventors completed the present invention.

That is, the present invention relates to an oxetane compound containing a (meth)acryloyl group and production method thereof as shown in the following items 1 to 6.

1. An oxetane compound containing a (meth)acryloyl group, which is represented by formula (1) below.

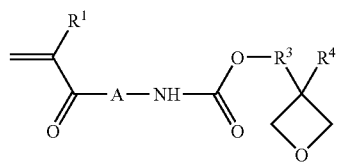

(1)

(In the formula, $R^1$ represents a hydrogen atom or a methyl group, A represents —$OR^2$— or a bond, $R^2$ represents a divalent hydrocarbon group which may contain an oxygen atom in the main chain, $R^3$ represents a linear or branched alkylene group having 1 to 6 carbon atoms, and $R^4$ represents a linear or branched alkyl group having 1 to 6 carbon atoms.)

2. The oxetane compound containing a (meth)acryloyl group as described in above 1, which is a compound represented by formula (2) below.

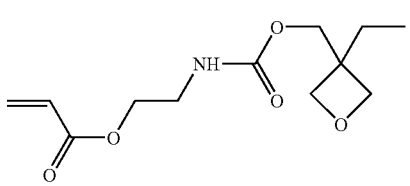

(2)

3. The oxetane compound containing a (meth)acryloyl group as described in 1 above, which is a compound represented by formula (3) below.

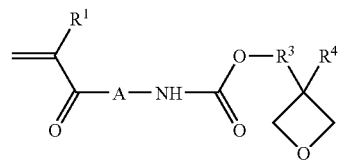

(In the formula, $R^1$ represents a hydrogen atom or a methyl group, A represents —$OR^2$— or a bond, and $R^2$ represents a divalent hydrocarbon group which may contain an oxygen atom in the main chain, $R^3$ represents an alkylene group having 1 to 6 carbon atoms, and $R^4$ represents an alkyl group having 1 to 6 carbon atoms.)

$R^1$ represents a hydrogen atom or a methyl group, and when $R^1$ is a hydrogen atom, the radical polymerization rate is higher. On the other hand, when $R^1$ is a methyl group, stability of the compound is increased, thereby providing a good handleability.

A represents —$OR^2$— or a bond. $R^2$ represents a divalent hydrocarbon group which may contain an oxygen atom in the main chain. Examples of such a divalent hydrocarbon group include alkylene group having 2 to 12 carbon atoms, oxyalkylene group having 2 to 12 carbon atoms, and arylene group having 6 to 12 carbon atoms. Specific examples thereof include —$(CH_2)_2$—, —$(CH_2)_3$—, —$(CH_2)_4$—, —$(CH_2)_5$—, —$CH(CH_3)CH_2$—, —$CH_2CH_2OCH_2CH_2$—, —$(CH_2CH_2O)_2CH_2CH_2$—, —$(CH_2CH_2O)_3CH_2CH_2$—, —$CH_2CH(CH_3)OCH_2CH(CH_3)$—, —$(CH_2CH(CH_3)O)_2CH_2CH(CH_3)$—, —$(CH_2CH(CH_3)O)_3CH_2CH(CH_3)$—, —$CH_2CH_2CH_2CH_2OCH_2CH_2CH_2CH_2$—, —$(CH_2CH_2CH_2CH_2O)_2CH_2CH_2CH_2CH_2$—, —$(CH_2CH_2CH_2CH_2O)_3CH_2CH_2CH_2CH_2$—, p-phenylene group and m-phenylene group. Among them, —$(CH_2)_2$— is preferable.

$R^3$ represents a linear or branched alkylene group having 1 to 6 carbon atoms. Examples of $R^3$ include methylene group, ethylene group, propylene group, butylene group, pentylene group and hexylene group. Among them, methylene group and ethylene group are particularly preferred from the view point of easy availability of raw materials.

$R^4$ represents a linear or branched alkyl group having 1 to 6 carbon atoms. Examples of $R^4$ include methyl group, ethyl group, n-propyl group, n-butyl group, sec-butyl group, tert-butyl group, n-pentyl group and n-hexyl group. Among them, methyl group and ethyl group are particularly preferred from the view point of easy availability of raw materials.

Among compounds represented by formula (1), particularly preferred examples include compounds represented by formula (2), formula (3) and formula (4).

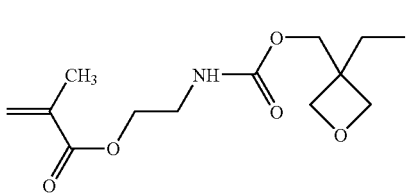

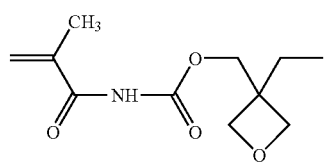

4. The oxetane compound containing a (meth)acryloyl group as described in 1 above, which is a compound represented by formula (4) below.

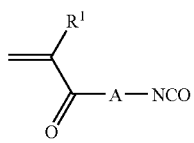

5. A production method of an oxetane compound containing a (meth)acryloyl group, wherein an isocyanate compound containing a (meth)acryloyl group represented by formula (5) below is reacted with an oxetane compound containing a hydroxyl group represented by formula (6) below.

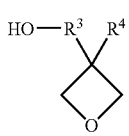

(In the formula, $R^1$ represents a hydrogen atom or a methyl group, A represents —$OR^2$— or a bond, and $R^2$ represents a divalent hydrocarbon group which may contain an oxygen atom in the main chain.)

HO—$R^3$ $R^4$
(6)

(In the formula, $R^3$ represents a linear or branched alkylene group having 1 to 6 carbon atoms, and $R^4$ represents a linear or branched alkyl group having 1 to 6 carbon atoms.)

6. The production method of an oxetane compound containing a (meth)acryloyl group as described in above 5, wherein a tertiary amine or a tin compound is used as catalyst.

DETAILED DESCRIPTION OF THE INVENTION

The present invention is hereinafter described in detail.

1. Oxetane Compound Containing a (meth)acryloyl Group

The oxetane compound containing a (meth)acryloyl group of the present invention is represented by formula (1) below.

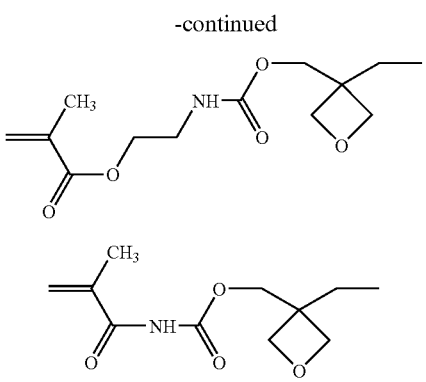

(3)

(4)

2. Production Method of Oxetane Compound Containing (meth)acryloyl Group

The oxetane compound containing a (meth)acryloyl group of the present invention can be obtained by reacting an isocyanate compound containing a (meth)acryloyl group with an oxetane compound containing a hydroxyl group.

2-1. Isocyanate Compound Containing a (meth)acryloyl Group

The isocyanate compound containing a (meth)acryloyl group which is used in the present invention is a compound represented by formula (5) below.

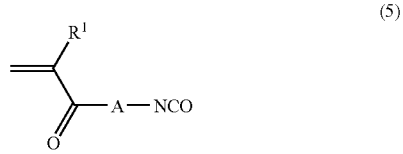

(5)

Same as defined in formula (1), $R^1$ represents a hydrogen atom and a methyl group, A represents —$OR^2$— or a bond, and $R^2$ represents a divalent hydrocarbon group which may contain an oxygen atom in the main chain.

Examples of compound represented by formula (5) include 1-(meth)acryloyloxymethyl isocyanate, 2-(meth)acryloyloxyethyl isocyanate, 3-(meth)acryloyloxypropyl isocyanate, 4-(meth)acryloyloxybutyl isocyanate, 6-(meth)acryloyloxyhexyl isocyanate, 10-(meth)acryloyloxydecyl isocyanate, 2-(meth)acryloyloxy-2-methyl-ethyl isocyanate, 2-(meth)acryloyloxy-1-methyl-ethyl isocyanate, 2-(meth)acryloyloxy-1,1-dimethyl-etyl isocyanate, 4-(meth)acryloyloxyphenyl isocyanate, 3-(meth)acryloyloxyphenyl isocyanate and (meth)acryloyl isocyanate.

2-2. Oxetane Compound Containing a Hydroxyl Group

The oxetane compound containing a hydroxyl group which is used in the present invention is a compound represented by formula (6).

(6)

$R^3$, which has the same meaning as defined in formula (1), represents an alkylene group having 1 to 6 carbon atoms, and $R^4$, which has the same meaning as defined in formula (1), represents an alkyl group having 1 to 6 carbon atoms.

Examples of compound represented by formula (6) include 3-methyl-3-hydroxymethyloxetane, 3-ethyl-3-hydroxymethyloxetane, 3-n-propyl-3-hydroxymethyloxetane, 3-isoprolyl-3-hydroxyymethyloxetane, 3-methyl-3-hydroxyethyloxetane, 3-ethyl-3-hydroxyethyloxetane, 3-n-propyl-3-hydroxyethyloxetane, 3-isopropyl-3-hydroxyethyloxetane, 2-methyl-3-hydroxymethyloxetane, 2-ethyl-3-hydroxymethyloxetane, 2,3-dimethyl-3-hydroxymethyloxetane, 2,4-dimethyl-3-hydroxymethyloxetane, 2,3,4-trimethyl-3-hydroxymethyloxetane, 3-ethyl-2-methyl-3-hydroxymethyloxetane, 3-ethyl-2,4-dimethyl-3-hydroxymethyloxetane, 3-methyl-3-(2-hydroxyethoxymethyl)oxetane, and 3-ethyl-3-(2-hydroxyethoxymethyl)oxetane. Among them, 3-methyl-3-hydroxymethyloxetane and 3-ethyl-3-hydroxymethyloxetane are particularly preferred from the viewpoint of costs and versatility.

2-3. Production Method

The oxetane compound containing a (meth)acryloyl group can be obtained by reacting an isocyanate compound containing a (meth)acryloyl group represented by formula (5) with an oxetane compound containing a hydroxyl group represented by formula (6).

As a reaction catalyst, known catalysts forming a urethane bond can be used. Examples of such a catalyst include tertiary amines (such as triethylamine, triethylenediamine and 1,8-diazabicyclo[5.4.0]undecene) and organic tin compounds (such as dibutyltin dilaurate and tin octylate).

As reaction solvent, any organic catalyst which is inactive with isocyanate group can be employed. Examples of such a catalyst include benzene, toluene, xylene, tetrahydrofuran, dibutyl ether, diethylene glycol dimethyl ether, ethylene glycol diethyl ether, propylene glycol monomethyl ether acetate, propylene glycol monoethyl ether acetate, diethylene glycol ethyl ether acetate, methyl methoxypropionate, ethyl methoxypropionate, methyl ethoxypropionate, ethyl ethoxypropionate, ethyl acetate, isoamyl acetate, acetone, methylethyl ketone, cyclohexanone, N,N-dimethylformamide and N-methylpyrrolidone.

The reaction temperature is generally 0 to 120° C., preferably 20 to 100° C., more preferably 30 to 80° C. If the temperature is less than 0° C., the reaction rate is very low. If the temperature exceeds 120° C., polymerization occurs, which is unpreferable.

The molar ratio of isocyanate compound:oxetane compound at the time of reaction is 1:0.90 to 1.10, preferably 1:0.95 to 1.05. When the ratio is less than 0.90, storage stability when the reaction product is used as material for acrylic copolymer decreases. On the other hand, when the ratio exceeds 1.10, the oxetane compound which excessively remains unreacted in the reaction product unpreferably deteriorates properties of the reaction product for use as material for acrylic copolymer.

Termination of reaction between an isocyanate compound containing a (meth)acryloyl group and an oxetane compound containing a hydroxyl group can be confirmed by disappearance of absorption of isocyanate group observed by using an infrared spectrophotometer. The reaction solution after termination of the reaction is washed with demineralized water, the organic solvent layer is dried, and the organic solvent is removed by using an evaporator, a vacuum pump or the like, to thereby obtain a crude product, which may be subjected to purification through column chromatography or the like when necessary.

3. Other Aspects

It is preferable that the oxetane compound containing a (meth)acryloylgroup of the present invention be preserved after adding a radical polymerization inhibitor for the purpose of improving thermal stability of the compound. Examples of radical polymerization inhibitor include benzoquinone, phenol, p-methoxyphenol, 2,6-di-t-butyl-p-cresol, butylhydroxyanisol and phenothiazine.

BEST MODE FOR CARRYING OUT THE INVENTION

The present invention is hereinafter explained by referring to Examples, however, the present invention is by no means limited to the Examples.

The purity of the product was measured by using high-performance liquid chromatography as shown below.

Column: Shodex 5C84E (manufactured by SHOWA DENKO K.K.),

Eluant composition: acetonitrile/water=2/1 (volume ratio) 2 mM tetra-n-butylammonium perchlorate Pump: LC-10AD (manufactured by Shimadzu Corporation), Eluant flow rate: 1.0 ml/minute, Temperature: 40° C., Detector: UV detector SPD-M10AVP (manufactured by Shimadzu Corporation), Detection wavelength: 210 nm.

EXAMPLE 1

Preparation of Compound Represented by Formula (2)

Into a 100 mL four-necked flask, 10.0 g of 2-acryloyloxyethyl isocyanate(manufactured by SHOWA DENKO K.K. (70.9 mmol), 8.24 g of 3-ethyl-3-hydroxymethyloxetane (manufactured by UBE INDUSTRIES, LTD., product name: Ethanacol EHO) (70.9 mmol), 0.04 g of dibutyltin dilaurate (manufactured by TOKYO KASEI KOGYO CO., LTD.) and 44.5 g of ethyl acetate were charged. A thermometer and a condenser were equipped to the flask, and the flask was heated to 55° C. in an oil bath. Stirring was performed by using a magnetic stirrer. After 4 hours' reaction, disappearance of absorption of isocyanate group was confirmed by using an infrared spectrophotometer (manufactured by JASCO Corporation, product code: FT-IR/8000 (hereinafter, simply referred to as "FT-IR")), and the reaction solution was washed with demineralized water twice and then the organic layer was dried over anhydrous magnesium sulfate. Further, ethyl acetate was removed by using an evaporator and a vacuum pump to thereby obtain 14.68 g of a crude product having a purity of 94.9%.

5.0 g of the crude product was subjected to purification through column chromatography with silica gel (manufactured by Wako Pure Chemical Industries, Ltd., product name: Wakogel C-200) and solvent composed of n-hexane:ethyl acetate=2:1 (volume ratio) and then condensed. Subsequently, the product was subjected to high-performance liquid chromatography (hereinafter, simply referred to as "LC"), to thereby obtain a purified product having a purity of 98.0%.

Figure 1:
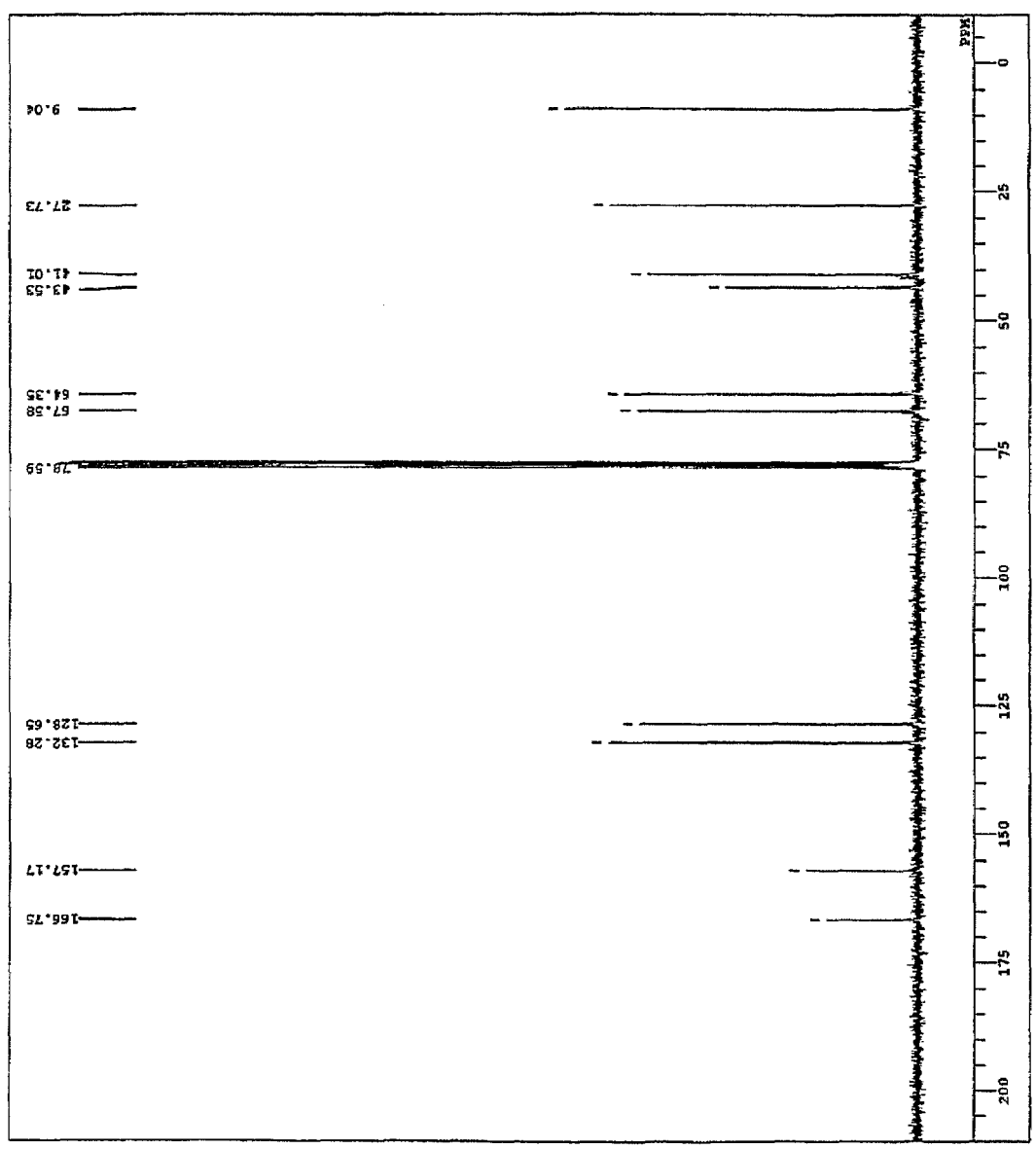
FIG. 1 is a chart showing results of $^{13}$C-NMR measurement on the compound in Example 1.

The obtained product was subjected to $^{13}$C-NMR spectrum measurement by using magnetic nuclear resonance analyzer (manufactured by JEOL, product code: JNM-AL400) (hereinafter, referred to as "NMR") in heavy chloroform. The resulting $^{13}$C-NMR chart is shown in FIG. 1. In attribution of the peaks in the chart, the purified product was confirmed to be represented by formula (2).

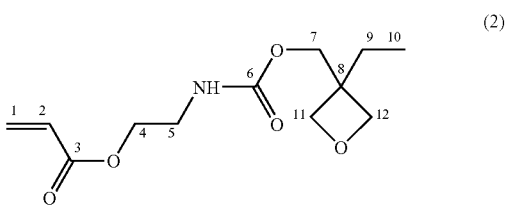

The peaks in the chart of FIG. 1 and attributions are shown below.

9.0 ppm: carbon atom in methyl group at 10, 27.7 ppm: carbon atom in methylene group at 9

41.0 ppm: carbon atom in methylene group at 5

43.5 ppm: quaternary carbon atom at 8

64.4 ppm: carbon atom in methylene group at 4

67.6 ppm: carbon atom in methylene group at 7

78.6 ppm: carbon atom in methylene groups at 11 and 12

128.7 ppm: carbon atom at 1

132.3 ppm: carbon atom at 2

157.2 ppm: carbon atom in carbonyl group at 6

166.8 ppm: carbon atom in carbonyl group at 3

EXAMPLE 2

Preparation of Compound Represented by Formula (3)

Into a 200 mL four-necked flask, 17.15 g of 2-methacryloyloxyethyl isocyanate(product name: karenz MOI, manufactured by SHOWA DENKO K.K. (111 mmol), 12.85 g of 3-ethyl-3-hydroxymethyloxetane (111 mmol), 0.06 g of dibutyltin dilaurate and 70.0 g of ethyl acetate were charged. A thermometer and a condenser were equipped to the flask, and the flask was heated to 55° C. in an oil bath. Stirring was performed by using a magnetic stirrer. After 6 hours' reaction, disappearance of absorption of isocyanate group was confirmed by using an FT-IR, and the reaction solution was washed with demineralized water twice and then the organic layer was dried over anhydrous magnesium sulfate. Further, ethyl acetate was removed by using an evaporator and a vacuum pump to thereby obtain 28.06 g of a crude product having a purity of 94.9%.

5.0 g of the obtained crude product was purified in the same manner as in Example 1 to thereby obtain a purified product having a purity of 98.3%.

The purified product was subjected to 13C-NMR measurement. The resulting $^{13}$C-NMR chart was shown in FIG. 2. In attribution of the peaks in the chart, the purified product was confirmed to be represented by formula (3).

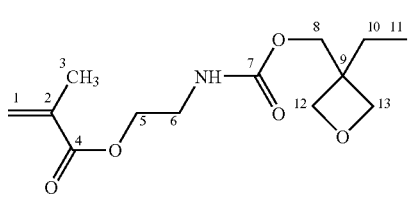

Figure 2:
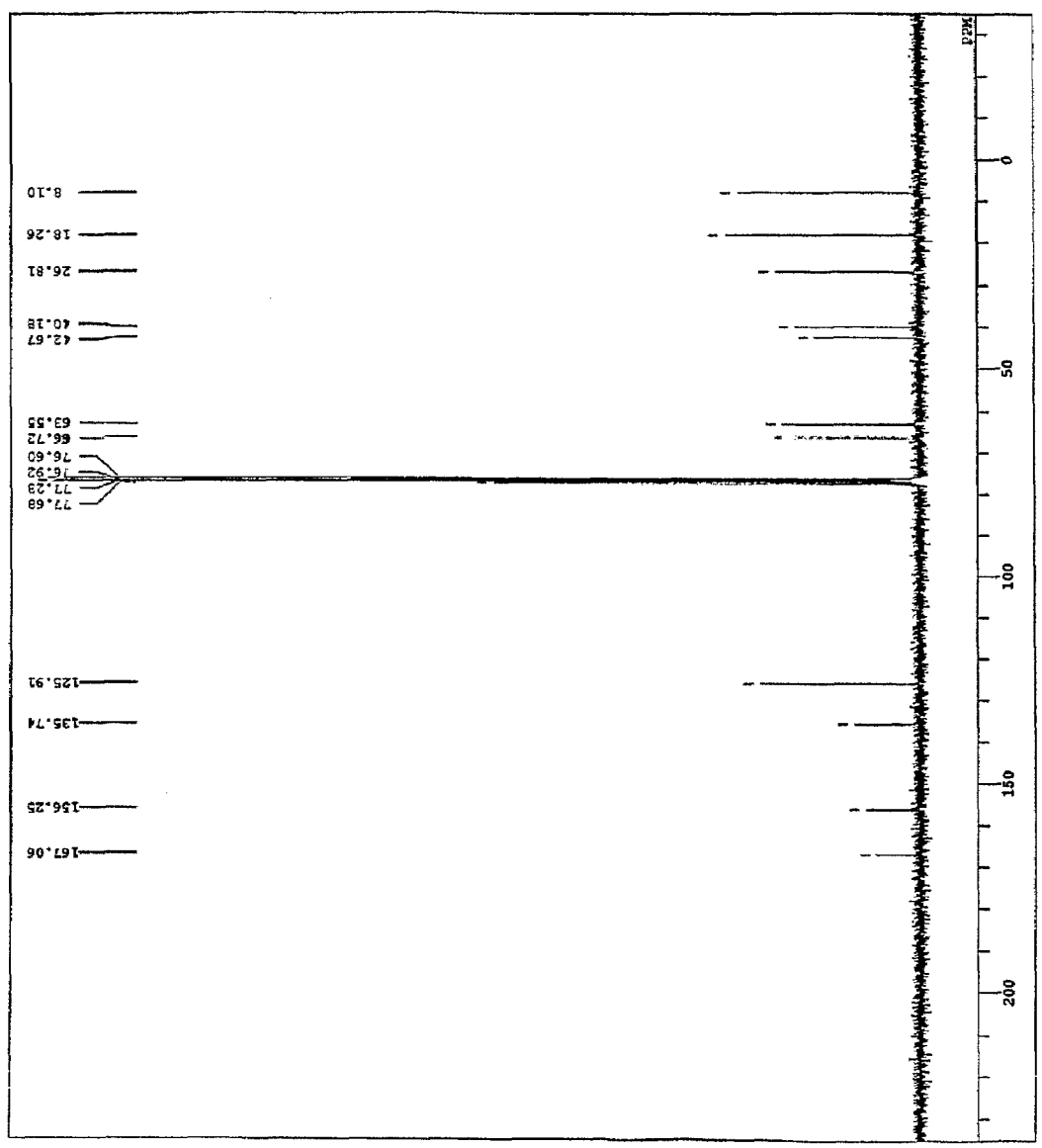
FIG. 2 is a chart showing results of $^{13}$C-NMR measurement on the compound in Example 2.

The peaks in the chart of FIG. 2 and attributions are shown below.
8.1 ppm: carbon atom in methyl group at 11
18.3 ppm: carbon atom in methyl group at 3,
26.8 ppm: carbon atom in methylene group at 10,
40.2 ppm: carbon atom in methylene group at 6,
42.7 ppm: quaternary carbon atom at 9,
63.6 ppm: carbon atom in methylene group at 5,
66.7 ppm: carbon atom in methylene group at 8,
77.7 ppm: carbon atom in methylene groups at 12 and 13,
125.9 ppm: carbon atom at 1,
135.7 ppm: carbon atom at 2,
156.3 ppm: carbon atom at carbonyl group at 7,
167.1 ppm: carbon atom at carbonyl group at 4.

INDUSTRIAL APPLICABILITY

Since the oxetane compound containing a (meth)acryloyl group of the present invention has a high copolymerizability with other ethylenically unsaturated compounds, the compound can be used for synthesis of various acrylic copolymers and can be anticipated to be a substitution for epoxy resin.

The invention claimed is:

1. An oxetane compound containing a (meth)acryloyl group, which is represented by formula (1) below

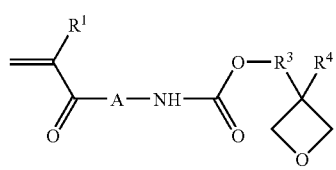

wherein $R^1$ represents a hydrogen atom or a methyl group, A represents —$OR^2$— or a bond, $R^2$ represents a divalent hydrocarbon group which may contain an oxygen atom in the main chain, $R^3$ represents a linear or branched alkylene group having 1 to 6 carbon atoms, and $R^4$ represents a linear or branched alkyl group having 1 to 6 carbon atoms.

2. The oxetane compound containing a (meth)acryloyl group claimed in claim 1, which is a compound represented by formula (2) below

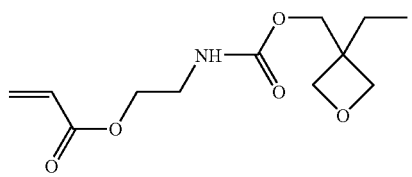

3. The oxetane compound containing a (meth)acryloyl group as claimed in claim 1, which is a compound represented by formula (3) below

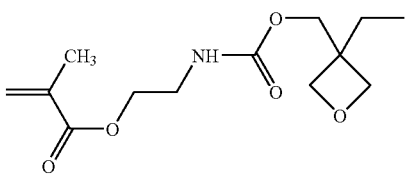

4. The oxetane compound containing a (meth)acryloyl group as claimed in claim 1, which is a compound represented by formula (4) below

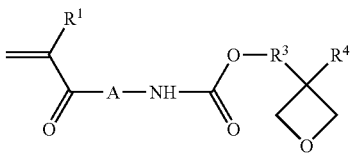

5. A production method of a compound represented by formula (1) below (1)

wherein $R^1$ represents a hydrogen atom or a methyl group, A represents —$OR^2$— or a bond, $R^2$ represents a divalent hydrocarbon group which may contain an oxygen atom in the main chain, $R^3$ represents a linear or branched alkylene group having 1 to 6 carbon atoms, and $R^4$ represents a linear or branched alkyl group having 1 to 6 carbon atoms, wherein an isocyanate compound containing a (meth)acryloyl group represented by formula (5) below is reacted with an oxetane compound containing a hydroxyl group represented by formula (6) below

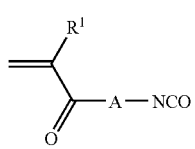

wherein $R^1$ represents a hydrogen atom or a methyl group, A represents —$OR^2$— or a bond, and $R^2$ represents a divalent hydrocarbon group which may contain an oxygen atom in the main chain,

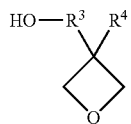
(6)

wherein $R^3$ represents a linear or branched alkylene group having 1 to 6 carbon atoms, and $R^4$ represents a linear or branched alkyl group having 1 to 6 carbon atoms, where the molar ratio of the isocyanate to oxetane at the time of reaction is 1:0.90 to 1:1.10.

6. The production method of an oxetane compound containing a (meth)acryloyl group as claimed in claim 5, wherein a tertiary amine or a tin compound is used as catalyst.

* * * * *